US00PP26165P3

(12) United States Plant Patent
Olesen

(10) Patent No.: US PP26,165 P3
(45) Date of Patent: Dec. 1, 2015

(54) SHRUB ROSE PLANT NAMED 'POULREN021'

(50) Latin Name: ***Rosa* hybrid**
Varietal Denomination: Poulren021

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 14 days.

(21) Appl. No.: 13/986,912

(22) Filed: Jun. 14, 2013

(65) Prior Publication Data

US 2014/0373201 P1 Dec. 18, 2014

(51) Int. Cl.
*A01H 5/02* (2006.01)

(52) U.S. Cl.
USPC ..... Plt./102

(58) Field of Classification Search
USPC ..... Plt./102, 108
See application file for complete search history.

(56) References Cited

PUBLICATIONS

Poulsen Roser A/S (retrieved from a Google search on Oct. 6, 2014 at <http://www.poulsenroser.com/assortment/rose-collections/renaissance/aya.aspx>).*

* cited by examiner

*Primary Examiner* — Keith O. Robinson

(57) ABSTRACT

A new garden rose plant of the Shrub class which has abundant, red-purple flowers and attractive foliage. This new and distinct variety has shown to be uniform and stable in the resulting generations from asexual propagation.

2 Drawing Sheets

Botanical designation: *Rosa* hybrid.
Variety denomination: 'Poulren021'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2001 and the resulting seeds were planted in a controlled environment in Fredensborg, Denmark. The new variety, named 'Poulren021', originated as a single seedling from the stated cross.

The new variety may be distinguished from its male pollen parent and female seed parent primarily by flower coloration and growth habit. The female seed parent is about 150 cm in height, while 'Poulren021' is about 90 cm in height. The male pollen parent has flowers which are generally Red Purple 58C while the claimed plant has a flower color of Red-Purple Group 61C.

The objective of the hybridization of this rose variety was to create a new and distinct variety for garden use with unique qualities, such as:

1. Uniform and abundant red purple flowers;
2. Vigorous, but compact growth when propagated both as a budded rose and on its own roots;
3. Exceptional disease resistance; and
4. Flowers with strong fragrance.

This combination of qualities is not present in previously available commercial cultivars of this type, known to the inventor, and distinguish 'Poulren021' from all other varieties of which we are aware.

As part of the rose development program, Mogens N. Olesen germinated the seeds from the aforementioned hybridization during winter of 2001 and conducted evaluations on the resulting seedlings in a controlled environment in Fredensborg, Denmark. 'Poulren021' was selected in the spring of 2002 by the inventor as a single plant from the progeny of the aforementioned hybridization.

Asexual reproduction of 'Poulren021' by traditional budding and rooted cuttings was first done by Mogens N. Olesen in the nursery in Fredensborg, Denmark in July, 2002. This initial and other subsequent asexual propagations conducted in controlled environments have demonstrated that the characteristics of 'Poulren021' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren021'.

Specifically illustrated in FIG. 1 of the drawing are flowers at various stages of development, flower petals detached, sepals and reproductive flower parts.

Figure 1:
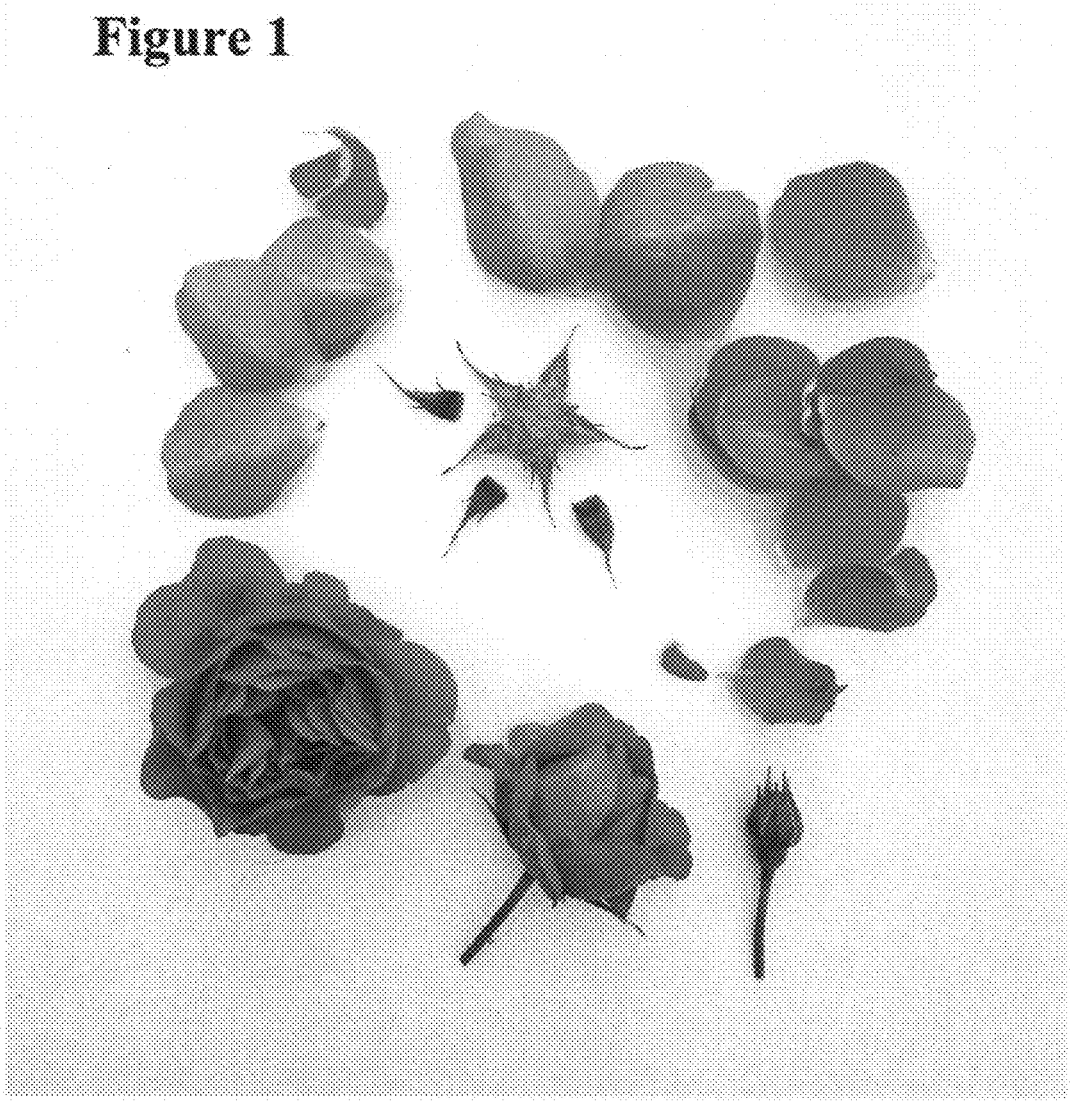
Figure 2:
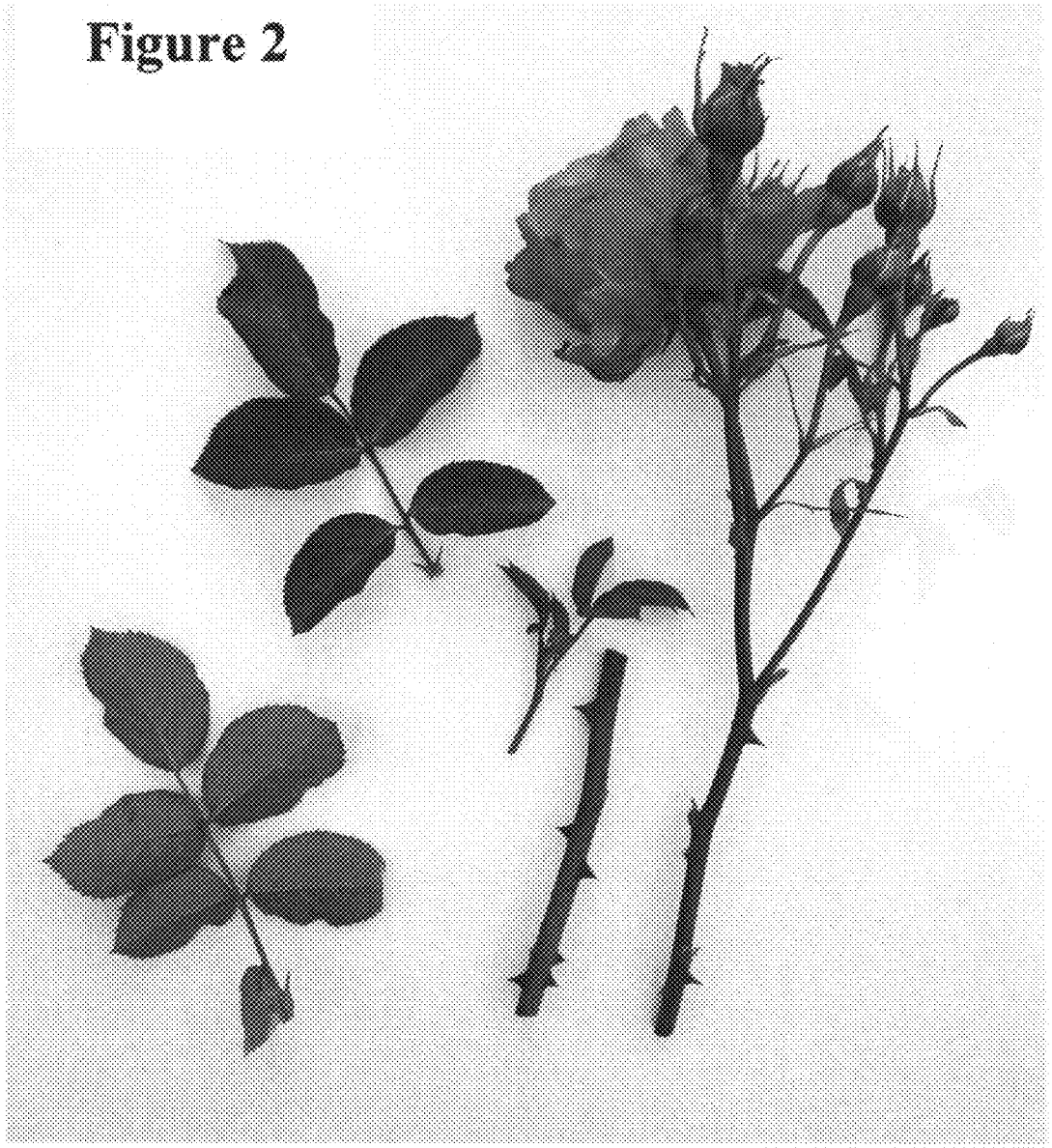
FIG. 2 shows a flowering branch, flower buds, bare stems, mature and juvenile leaves.

Illustrated plants are 2 years of age.

DETAILED DESCRIPTION OF THE VARIETY

The following is a description of 'Poulren021', as observed in its growth in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulen007', U.S. Plant Pat. No. 15,197 are compared to 'Poulren021' in Chart 1.

CHART 1

| | 'Poulren021' | 'Poulen007' |
|---|---|---|
| Growth height | 90 cm | 100 to 150 cm |
| Flower Diameter | 100 mm | 90 mm |
| General Tonality of Flower Color | Red-Purple Group 61C | Red-Purple Group 61A |

FLOWER AND FLOWER BUD

Blooming habit: Continuous.

Flower bud:

*Size.*—Upon opening, 30 mm in length from base of receptacle to end of bud. Bud diameter is 17 mm.

*Bud form.*—Ovoid.

*Bud color.*—As sepals divide petals are Red Group 42A.

*Sepal inner surface.*—Color: Green Group 138B. Surface: Smooth, with moderate pubescence.

*Sepal outer surface.*—Color: Yellow-Green Group 144A, with intonations of Greyed-Red Group 178A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—26 mm long by 10 mm wide.

*Receptacle.*—Texture: Smooth. Size: 10 mm in height by 10 mm wide. Color: Yellow-Green Group 144A. Anthocyanic pigments the color of Greyed Red Group 178A observed. Shape: Campanulate.

*Pedicel.*—Surface: Somewhat rough with small prickles and stipitate glands. Length: 35 to 45 mm. Diameter: 3 to 4 mm. Color: Yellow-Green Group 144C. Anthocyanic pigments the color of Greyed-Red Group 181A observed. Small prickles are Greyed-Red Group 178B. Strength: Strong.

*Peduncle.*—Length: 30 to 40 mm. Diameter: About 3 mm. Color: Yellow-Green Group 144C with strong intonations of Greyed-Red Group 181B. Texture: Smooth. Strength: Strong.

Flower bud development: Flower buds are borne in clusters of 5 to 11 flower buds per stem, resembling a corymb. It total, 'Poulren021' displays about 50 flowers in full bloom.

Flower bloom:

*Fragrance.*—Strong perfume.

*Duration.*—The blooms have a duration on the plant of approximately 7 to 10 days. Petals fall cleanly away from plant after flowers have fully matured.

*Size.*—Flower diameter is 100 mm when open. Flower depth is 50 mm.

*Flower shape.*—General shape is a quartered rosette with many overlapping petals packed into quarter sections.

*Shape of flower, side view.*—The upper portion is flat, the lower portion is concave.

Petalage: Under normal conditions, flowers have 60 petals total, 15 of which are petaloids.

General tonality of flower: Open flowers are Red-Purple Group 61C. Tonality remains as the flower ages.

Petal color:

*Upon opening, outer petals.*—Upper surface: Red-Purple Group N57C. Lower surface: Red-Purple Group N57D to N57C. Splashed with intonations of Red-Purple Group 62B.

*Upon opening, inner petals.*—Upper surface: Red-Purple Group N57C. Lower surface: Red-Purple Group N57D to N57C. Splashed with intonations of Red-Purple Group 62B.

*Basal petal spots, upon opening.*—Upper surface: Yellow Group 11D. Lower surface: Yellow Group 11D.

*After opening, outer petals.*—Upper surface: Red-Purple Group N57C. Lower surface: Red-Purple Group N57D to N57C. Splashed with intonations of Red-Purple Group 62B.

*Upon opening, inner petals.*—Upper surface: Red-Purple Group N57C. Lower surface: Red-Purple Group N57D to N57C. Splashed with intonations of Red-Purple Group 62B.

*Basal petal spots, after opening.*—Upper surface: Yellow Group 11D. Lower surface: Yellow Group 11D.

Petals:

*Petal reflex.*—Absent.

*Margin.*—Entire and uniform. Occasionally there is a cleft at the apex. Margins are moderately undulated.

*Shape.*—Generally broad elliptic. Apex shape: Emarginate. Base shape: Acute.

*Size.*—55 mm (l) 50 mm (w).

*Texture.*—Smooth.

*Thickness.*—Average.

Petaloids:

*Size.*—35 mm (l) by 20 mm (w).

*Quantity.*—About 15.

*Shape.*—Asymmetric. Base is acute. Apex is rounded.

*Color.*—Upper surface is Red-Purple Group N57C. Lower surface is Red-Purple Group N57D to N57C. Splashed with intonations of Red-Purple Group 62B. Basal petaloid spots are Yellow Group 11D.

Reproductive organs:

*Pollen.*—None observed.

*Anthers.*—Size: 3 mm in length. Color: Yellow Group 11B with margins Yellow-Orange Group 22A. Quantity: 45 on average.

*Filaments.*—Color: Red-Purple Group 63B. Length: 8 mm.

*Pistils.*—Length: 4 mm. Quantity: 25 on average.

*Stigmas.*—Color: Greyed-Yellow Group 160A.

*Styles.*—Color: Yellow-Green Group 150C.

*Location of stigmas.*—Inferior in location relative to the length of the filaments and the height of the anthers.

*Hips.*—None Observed.

PLANT

Plant growth: Upright. Plants are 90 cm in height, and 90 cm wide.

Stems:

*Color.*—Juvenile growth: Yellow-Green Group 146C with intonations of Greyed-Orange Group 176A. Mature growth: Yellow-Green Group 146B.

*Length.*—On average, canes are 50 cm from the base of the plant to the flowering portion.

*Diameter.*—8 mm.

*Internodes.*—On mature canes, there is an average distance of 35 to 40 mm between nodes.

*Surface texture.*—Young wood: Smooth. Older wood: Smooth.

Long prickles:

*Incidence.*—12 prickles per 10 cm of stem.

*Size.*—Average length of prickles on mature stems is 8 mm.

*Shape.*—Upper portion is concave. Lower portion is concave.

*Color.*—Juvenile prickles: Greyed-Orange Group 176A. Mature prickles: Brown Group 200B.

Plant foliage:

*Compound leaf.*—145 mm (l)×110 (w).

*Quantity.*—2 to 3 leaves per 10 cm of stem.

*Leaf bearing angle to the stem.*—60 degrees.

*Color of juvenile foliage.*—Upper side: Yellow-Green Group 146B with margins Greyed-Purple Group 183A. Lower side: Greyed-Purple Group 183B.

*Color of mature foliage.*—Upper side: Yellow-Green Group 147A. Lower side: Yellow-Green Group 147B.

Plant leaves and leaflets:

*Stipules.*—Size: 15 mm in length. Quantity: 2 per compound leaf. Shape: Linear, slightly broad based with outward extending apices. Margins: Finely serrated with few stipitate glands. Color: Green Group 143B.

*Petiole.*—Length: 40 mm. Diameter: 2 mm. Texture: Smooth.

*Upper surface.*—Color: Yellow-Green Group 146B with light intonations of Greyed-Purple Group 183B where leaflets meet the rachis. Texture: Smooth.

*Lower surface.*—Color: Yellow-Green Group 144B. Observations: small Greyed-Purple prickles observed. Texture: Smooth.

*Rachis.*—Length: 45 mm. Upper surface: Yellow-Green Group 146B with light intonations of Greyed-Purple Group 183B where leaflets meet the rachis. Lower surface: Color: Yellow-Green Group 144B. Observations: Small Greyed-Purple prickles observed.

*Leaflet.*—Quantity: Normally, 5 leaflets found of leaves at mid stem. Margins: Serrated. Size: Average size of the terminal leaflet on normal leaves is 60 mm in length by 40 mm wide. Shape: Generally ovate. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa,* downy mildew *Peronospora sparsa,* rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the shrub rose class named 'Poulren021', substantially as illustrated and described herein, due to its abundant red purple flowers, disease resistance, and extended period of bloom.

* * * * *